(12) United States Patent
Hayashi et al.

(10) Patent No.: US 10,993,980 B2
(45) Date of Patent: May 4, 2021

(54) METHOD FOR TREATING ELECTROHYPERSENSITIVITY WITH A FERMENTED PAPAYA PREPARATION

(71) Applicant: Osato International Inc., Gifu (JP)

(72) Inventors: Yukiyasu Hayashi, Gifu (JP); Dominique Belpomme, Paris (FR)

(73) Assignee: Osato International Inc., Gifu (JP)

( * ) Notice: Subject to any disclaimer, the term of this patent is extended or adjusted under 35 U.S.C. 154(b) by 0 days.

(21) Appl. No.: 16/551,926

(22) Filed: Aug. 27, 2019

(65) Prior Publication Data

US 2020/0061140 A1 Feb. 27, 2020

(30) Foreign Application Priority Data

Aug. 27, 2018 (JP) .............................. JP2018-158529

(51) Int. Cl.
*A61K 36/185* (2006.01)
*A61K 36/31* (2006.01)
*A61P 25/00* (2006.01)

(52) U.S. Cl.
CPC .............. *A61K 36/31* (2013.01); *A61P 25/00* (2018.01)

(58) Field of Classification Search
None
See application file for complete search history.

(56) References Cited

U.S. PATENT DOCUMENTS

2016/0184377 A1* 6/2016 Hayashi .................... A61P 3/10
424/278.1

FOREIGN PATENT DOCUMENTS

| JP | 2011-041478 A | 3/2011 |
| WO | 2016/027333 A1 | 2/2016 |
| WO | 2016/027334 A1 | 2/2016 |

OTHER PUBLICATIONS

Marotta, F. et al. A 2 Year Double Blind RCT Followup Study with Fermented Papaya Preparation . . . Clinical Pharmacology & Biopharmaceutics vol. 6, 2017 (Year: 2017).*
Marotta F. et al. Functional Foods in Genomic Medicine . . . Acta Biomedica 83(1)21-29, 2012. (Year: 2012).*
Philippe et al., "Beneficial effects of a Fermented Papaya Preparation for the treatment of electrohypersensitivity self-reporting patients: results of a phase I-II clinical trial with special reference to cerebral pulsation measurement and oxidative stress analysis," Functional Foods in Health and Disease, 8 (2): 122-144 (2018).
Mild, ed., "Electromagnetic Hypersensitivity, Proceedings International Workshop on EMF Hypersensitivity," Prague, Czech Republic, Oct. 25-27, 2004, p. 16.
Bergqvist, ed., "Possible health implications of subjective symptoms and electromagnetic fields: A report prepared by a European group of experts for the European Commission, DG V," Arbete och Halsa, 1997: 19 (1997).
Santini et al., "Symptoms experienced by users of digital cellular phones: A study of a French engineering school," Electromagnetic Biology and Medicine, 21 (1): 81-88 (2002).
Roosli, "Radiofrequency electromagnetic field exposure and non-specific symptoms of ill health: A systematic review," Environmental Research, 107: 277-287 (2008).
Baliatsas et al., "Non-specific physical symptoms and electromagnetic field exposure in the general population: Can we get more specific? A systematic review," Environment International, 41: 15-28 (2012).
Hagstrom et al., "Electromagnetic hypersensitive Finns: Symptoms, perceived sources and treatments, a questionnaire study," Pathophysiology, 20: 117-122 (2013).
Belpomme et al., "Reliable disease biomarkers characterizing and identifying electrohypersensitivity and multiple chemical sensitivity as two etiopathogenic aspects of a unique pathological disorder," Reviews on Environmental Health, 30 (4): 251-271 (2015).
Aruoma et al., "Applications and bioefficacy of the functional food supplement fermented papaya preparation," Toxicology, 278 (1): 6-16 (2010).

\* cited by examiner

*Primary Examiner* — Ralph J Gitomer
(74) *Attorney, Agent, or Firm* — Morgan, Lewis & Bockius LLP

(57) ABSTRACT

Present disclosure provides a pharmaceutical composition or a preparation composition containing fermented papaya preparation as an active ingredient for treating a patient with electrohypersensitivity or relieving a symptom thought to be a symptom of the electrohypersensitivity, and methods of use thereof.

12 Claims, 3 Drawing Sheets

METHOD FOR TREATING ELECTROHYPERSENSITIVITY WITH A FERMENTED PAPAYA PREPARATION

TECHNICAL FIELD

The present disclosure relates to a pharmaceutical composition or a preparation composition for treating electrohypersensitivity, and methods of use thereof. Specifically, the present disclosure relates to a pharmaceutical composition for treating electrohypersensitivity that contains fermented papaya preparation as an active ingredient, a pharmaceutical composition and a preparation composition which are for a treatment for or relief from a decrease in brain blood flow, cognitive impairment, somnipathy, and/or fatigue. The present disclosure also relates to a method of treating electrohypersensitivity in a subject in need thereof, for example, electrohypersensitivity-bearing patients, comprising administering the above-mentioned pharmaceutical composition to the subject to obtain a normal recovery of their brain blood flow and neuronal function and the relief from cognitive impairment, somnipathy, and/or fatigue which occur in the subject.

BACKGROUND

In recent years, a source of radio waves and electromagnetic waves has diversified, the number of people suffering from hypersensitivity to electromagnetic waves and electromagnetic fields increases, generally called "electrohypersensitivity". Symptoms thereof vary from person to person, there is a wide range of severity, and some people who are affected will interfere with daily life.

According to World Health Organization (WHO), electrohypersensitivity (EHS) is also called idiopathic environmental intolerance (IEI) due to electromagnetic field (IEI-EMF) (Hansson Mild K, Repacholi M, van Deventer E, Ravazzani P, eds. 2006. Electromagnetic Hypersensitivity: Proceedings, International Workshop on EMF Hypersensitivity, Prague, Czech Republic, Oct. 25-27, 2004. Geneva (Switzerland): WHO Press. p. 16.). All the symptoms reported by these patients that may cause chronic insomnia, fatigue, hypersensitivity, and depression tendency occur each time they feel exposed to electromagnetic fields (Bergqvist U, Vogel E, Editors. Possible health implications of subjective symptoms and electromagnetic fields. A report prepared by a European group of experts for the European Commission, DGV. Arbete och Halsa, 1997:19. Swedish National Institute for Working Life, Stockholm, Sweden. http://www2.niwl.se/forlag/en/; Santini R, Seigne M, Bonhomme-Faivre L, Bouffet S, Defrasme E, Sage M. Symptoms experienced by users of digital cellular phones: a study of a French engineering school. Electromagn Biol Med. 2002, 21:81-88., Roosli M. Radiofrequency electromagnetic field exposure and non-specific symptoms of ill health: a systematic review. Environ Res. 2008, 107:277-287., Baliatsas C, Van Kamp I, Bolte J, Schipper M, Yzermans J, Lebret E. Non-specific physical symptoms and electromagnetic field exposure in the general population: can we get more specific? A systematic review. Environ Int. 2012, 41:15-28., and Hagstrom M1, Auranen J, Ekman R. Electromagnetic hypersensitive Finns: Symptoms, perceived sources and treatments, a questionnaire study. Pathophysiology. 2013, 20:117-122.).

On the other hand, "electrohypersensitivity" is considered to have no medical diagnostic criteria since WHO said that the existence of various symptoms is real but "there are no medical diagnostic criteria and there is no scientific basis that the symptoms are causally related to electromagnetic field exposure (WHO fact sheet no 292, December 2005)".

In recent years, the present inventors showed clinically that electrohypersensitivity that they also called electromagnetic field (EMF) intolerance syndrome (EMFIS), is related to a decrease in intracerebral tissue pulsation within the temporal lobes and can be characterized biologically by several blood biomarkers. They showed that the peripheral blood of the patients had several biological abnormalities including various degrees of oxidative stress, low grade inflammation, and autoimmune response. Thus, the present inventors hypothesized that this process can explain the opening of the blood brain barrier and a decrease of brain blood flow in temporal lobes of these patients (Belpomme D, Campagnac C, Irigaray P. Reliable disease biomarkers characterizing and identifying electrohypersensitivity and multiple chemical sensitivity as two etiopathogenic aspects of a unique pathological disorder. Rev Environ Health. 2015, 30: 251-271; Belpomme D, Hardell L, Belyaev I, Burgio E, Carpenter D O. Thermal and non-thermal health effects of low intensity non-ionizing radiation: An international perspective. Environ Pollut. 2018 November; 242(Pt A):643-658.).

A fermented papaya preparation (FPP) produced by fermenting immature fruits of *Carica papaya* (*Carica papaya* Linn) together with sugar with edible yeast increases maltose and maltotriose compared to a case of mixing with saliva and water.

Oral ingestion of the FPP is expected to increase the oligosaccharide to regulate an intestinal environment, and expected to suppress blood sugar elevation in type 2 diabetic patients, improve energy metabolism, and promote wound healing by enhancing immunity (Japanese Unexamined Patent Publication No. 2011-041478, PCT International Publication No. WO2016/027334, and PCT International Publication No. WO2016/027333). The FPP is also known to have antioxidant properties and to obtain effects on symptoms associated with aging (Aruoma O I, Hayashi Y, Marotta F, Mantello P, Rachmilewitz E, Montagnier L. Applications and bioefficacy of the functional food supplement fermented papaya preparation. Toxicology 278: 6-16, 2010.).

SUMMARY

While there is no definitive scientific proof that EMF exposure alone can cause electrohypersensitivity, the symptoms related to electrohypersensitivity certainly exist, and for patients suffering from the symptoms, establishment of a treatment thereof is needed. An object of the present disclosure is to provide a pharmaceutical composition or a preparation composition capable of treating a patient with electrohypersensitivity or relieving a symptom thought to be associated with the electrohypersensitivity.

The present inventor administered a fermented papaya preparation to patients who self-reports on "electrohypersensitivity". As a result, it was found that clinical improvement was seen in 50 to 60% of the entire sample of patients studied, among which 20 to 35% presented a major reduction of cognitive symptoms such as loss of short term memory, impaired concentration, and attention deficit in addition to a reduction in, insomnia and fatigue; the symptomatic improvement being associated with a significant normalization of pulsometric index (PI) measured by ultrasonic cerebral tomosphygmography (UCTS) in temporal lobes and with a significant normalization of blood test.

That is, the present disclosure relates, for example, to each of the following disclosures.

[1] A pharmaceutical composition for a treatment of electrohypersensitivity, the composition including: a fermented papaya preparation as an active ingredient.

[2] The pharmaceutical composition according to [1], which is for a suppression of a decrease in brain blood flow.

[3] The pharmaceutical composition according to [1], which is for a reduction of cognitive impairment, somnipathy, and/or fatigue.

[4] The pharmaceutical composition according to [3], in which the cognitive impairment includes loss of short term memory, impaired concentration, and attention deficit.

[5] A preparation composition for relief from a decrease in brain blood flow, cognitive impairment, somnipathy, and/or fatigue which are related to electrohypersensitivity, the composition including: a fermented papaya preparation as an active ingredient.

[6] A preparation composition for relief from clinical symptoms associated with electrohypersensitivity the composition including: a fermented papaya preparation as an active ingredient.

[7] The preparation composition according to [6], wherein the clinical symptoms associated with electrohypersensitivity comprise cognitive impairment, somnipathy, and/or fatigue.

[8] The pharmaceutical composition according to any one of [1] to [4] or the preparation composition according to any one of [5] to [7], in which a dose of the fermented papaya preparation is 0.5 to 30 g/day for adults weighing 70 kg.

[9] The method of treating electrohypersensitivity in a subject in need thereof, comprising administering the pharmaceutical composition according to any one of [1] to [4], and [8] or the preparation composition according to any one of [5] to [7], and [8].

[10] The method according to [9], in which the subject is human.

[11] The method according to [9] or [10], in which the subject is not diagnosed with type 2 diabetes.

[12] The method according to [11], in which the subject is not diagnosed with diabetes.

[13] A method for relief from clinical symptoms associated with electrohypersensitivity, comprising administering the pharmaceutical composition according to any one of [1] to [4], and [8] or the preparation composition according to any one of [5] to [7], and [8].

According to the composition and methods of the present disclosure, it is possible to relieve a symptom related to electrohypersensitivity, in particular, symptoms such as a decrease in brain blood flow, cognitive impairment, somnipathy, and/or fatigue.

DETAILED DESCRIPTION

Figure 1:
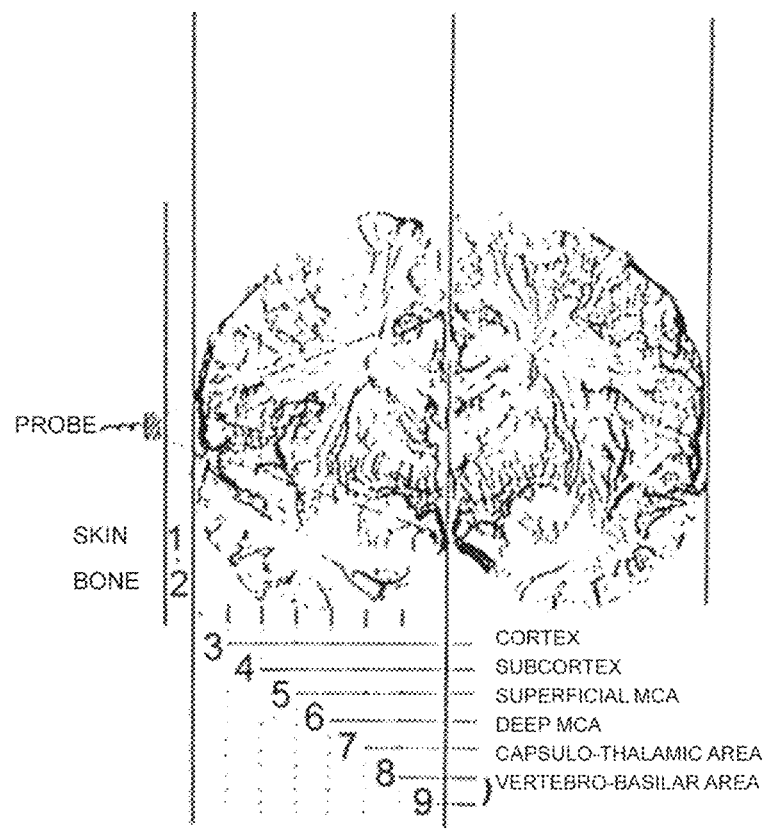
FIG. 1 is a schematic diagram showing the different middle cerebral artery (MCA)-dependent areas individualized in the temporal lobes for measurement of mean pulsometric index (PI) value by using UCTS.

A composition of the present disclosure includes an FPP as an active ingredient. The FPP is a fermented product derived from papaya, which is produced by fermenting immature fruits of Carica papaya (Carica papaya Linn) together with sugar with edible yeast as described above.

The FPP is preferably developed by Osato Research Institute, produced by OSATO Laboratory Inc., and sold by OSATO International, Inc. (Japanese Unexamined Patent Publication No. 2011-041478, Aruoma O I, Hayashi Y, Marotta F, Mantello P, Rachmilewitz E, Montagnier L. Applications and bioefficacy of the functional food supplement fermented papaya preparation. Toxicology 278: 6-16, 2010.). The FPP is available as "FPP Fermented Papaya Preparation" (trade name) or "Immun' Age" (trade name). The FPP is certified under ISO 9001: 2008, ISO 14001: 2004, ISO 22000: 2005, is produced at a factory that acquired FSSC 22000, the most stringent food safety standard in the Europe and America in HA Domestic No. 1, and is guaranteed in quality, environmental, and safety aspects.

A production method of the FPP is described in, for example, Japanese Unexamined Patent Publication No. 2011-041478. In analyzed by Japan Food Research Laboratories, the FPP includes 91.2 g of carbohydrate in 100 g of FPP and other small amounts of protein (0.3 g), lipid (0.2 g), potassium (14.9 mg) and water (8.5 g) (Lot No. 091; analysis test report dated May 27, 2014).

The FPP may be appropriately prepared into various forms such as granules, powders, and fine granules so as to be suitable for oral ingestion, and it is possible to appropriately add additives such as excipients, binders, and lubricants when preparing thereof.

A dose of FPP may be 0.5 to 30 g/day, is preferably 1 to 20 g/day, more preferably 3 to 15 g/day or 9 to 30 g/day, most preferably 3 to 9 g/day, 6 to 9 g/day, or 9 to 15 g/day, as an active ingredient, for adults weighing 70 kg. A dose of FPP may be at least 5, 10, 10, 20, 30, 40, 50, 60, 70, 80, 90, 100, 110, 120, 130, 140, 150, 160, 170, 180, 190, 200 or 250 mg/day/kg body weight. A dose of FPP may be 500, 450, 400, 350, 300, 250, 200, 150, 100, 90, 80, 70, 60, or 50 or less mg/day/kg body weight.

The composition of the present disclosure is effective in the treatment of electrohypersensitivity, that is, a treatment for or relief from symptoms related to the electrohypersensitivity. Electrohypersensitivity is an idiopathic environmental intolerance attributed to an electromagnetic field as described above, and refers to various clinical symptoms.

Electromagnetic waves comprise ionizing radiation including gamma rays, X rays, ultraviolet rays, and non-ionizing radiation including visible rays, infrared rays, radio waves in the order of short wavelength and low and extremely low frequency waves. In people complaining with "electrohypersensitivity", main causes of the symptoms thereof are the commercial power frequency (50/60 Hz) emitted from power transmission lines and household electrical appliances, and microwaves from mobile phones, DECT, Wifi and base station towers.

Although there is still not acknowledged diagnostic criteria for electrohypersensitivity, it can be diagnosed based not only on self-report of the patient and objective clinical symptoms but also mainly on objectives tests as described in Belpomme D, Campagnac C, Irigaray P. Reliable disease biomarkers characterizing and identifying electrohypersensitivity and multiple chemical sensitivity as two etiopathogenic aspects of a unique pathological disorder. Rev Environ Health. 2015, 30:251-271. Examples of symptoms related to or suspected to have relation with the electrohypersensitivity include skin symptoms such as tingling sensation, burning sensation, rash, redness, and tingling pain, and symptoms such as headache, fatigue, somnipathy, cognitive impairment, mental stress, muscle pain, dizziness, nausea, cardiac palpitations, and gastrointestinal disorders. For an objective specific diagnostic method, the electrohypersensitivity may be evaluated, for example, according to the criteria described in Examples.

The composition of the present disclosure may result in clinical improvement of electrohypersensitivity. For example, the decrease in the brain blood flow may be suppressed, and cognitive impairment, somnipathy and/or fatigue may be relieved. Examples of the cognitive impairment include loss of short-term memory, impaired concentration, and attention deficit. The present disclosure also is related to a method of treating electrohypersensitivity in a subject in need thereof, comprising administering the pharmaceutical composition or preparation composition described herein. For example, the subject may be human. The subject may not be diagnosed with type 2 diabetes or diabetes. The subject may not be in need of an antioxidant. The subject may not be diagnosed with any inflammatory disease. The subject may not be diagnosed with any immune disease.

EXAMPLES

The present inventors conducted the following clinical study for validation of effects of FPP on subjects who are patients self-reported on electrohypersensitivity. 32 EMFIS-bearing patients participated in this clinical study, among them, 26 and 16 persons were evaluated after 3 and 6 months of FPP treatment, respectively. Clinical evaluation was conducted during a specific face to face interview by using a validated pre-established questionnaire. Biological evaluation was performed by measuring intracerebral tissue pulsometric index (PI) in temporal lobes with ultrasonic cerebral tomosphygmography (UCTS), in addition to oxidative stress measurement, oxidative stress-related inflammation, and inflammation-related peripheral blood tests.

Materials and Methods

Study Inclusion Criteria

EMFIS was clinically defined on the basis of five criteria (Roosli M. Radiofrequency electromagnetic field exposure and non-specific symptoms of ill health: a systematic review. Environ Res. 2008, 107:277-287., Baliatsas C, Van Kamp I, Bolte J, Schipper M, Yzermans J, Lebret E. Non-specific physical symptoms and electromagnetic field exposure in the general population: can we get more specific? A systematic review. Environ Int. 2012, 41:15-28., Hagstrom M1, Auranen J, Ekman R. Electromagnetic hypersensitive Finns: Symptoms, perceived sources and treatments, a questionnaire study. Pathophysiology. 2013, 20:117-122., and Belpomme D, Campagnac C, Irigaray P. Reliable disease biomarkers characterizing and identifying electrohypersensitivity and multiple chemical sensitivity as two etiopathogenic aspects of a unique pathological disorder. Rev Environ Health. 2015, 30:251-271):

(1) Absence of known pathology accounting for the observed clinical symptoms;

(2) Reproducibility of symptoms under the presumed influence of EMFs, regardless of the incriminated source (radio-frequencies and/or hyper frequencies or low and/or extremely low frequencies);

(3) Regression or disappearance of clinical symptoms in the case of presumed EMF avoidance;

(4) Clinical symptoms compatible with those previously reported in EHS self-reporting patients in the scientific literature; and (5) Chronic evolution of symptoms.

Before inclusion in this clinical study, all patients had a general and neurological clinical test and a systematic general biological test, in order to exclude any EMFIS-non related pathology. Thus, in order to be included in the study, patients should have a normal carotidian and vertebral echodoppler, a normal magnetic resonance imaging (MRI) or computed tomography (CT) scan, and normal blood tests that are currently used, in particular hematologic, hepatic, and renal tests. Moreover, patients should be between 18 and 75 years old, have a body mass index between 18.5 and 25, normal peripheral blood pressure, normal fasting glycemia, no gluten and/or lactose/casein intolerance, and no multiple chemical sensitivity (MCS)-related pathology.

Moreover, all patients should have no history of pathologies such as cancer, Alzheimer disease, type II diabetes, and/or cardiovascular disease, and should be in a clinical active phase of EMFIS whether they have been treated or not treated previously. That is, according to a grading scale system used by the present inventors, grade 2 or 3 clinical symptoms was shown (see the section "Evaluation").

However, since clinical symptoms in so-called EHS patients are mainly subjectively expressed, two additional biological inclusion criteria to characterize objectively EMFIS bearing patients were used:

(1) A low mean tissue PI measured in areas of at least one temporal lobe by using UCTS (As previously reported, in EHS self-reporting patients, there is a low mean tissue PI in several areas of temporal lobes (Belpomme D, Campagnac C, Irigaray P. Reliable disease biomarkers characterizing and identifying electrohypersensitivity and multiple chemical sensitivity as two etiopathogenic aspects of a unique pathological disorder. Rev Environ Health. 2015, 30:251-271.)); and (2) Increase of at least one of three peripheral blood biomarkers previously identified as being possibly associated with EHS (Belpomme D, Campagnac C, Irigaray P. Reliable disease biomarkers characterizing and identifying electrohypersensitivity and multiple chemical sensitivity as two etiopathogenic aspects of a unique pathological disorder. Rev Environ Health. 2015, 30:251-271.): Increased histamine which is a mediator of inflammation; increased protein S100B which is a marker of oxidative stress-related BBB opening; and increased chaperone proteins Hsp27 and/or Hsp70 which are markers of heat-shock cell stress-related inflammation and/or immune response (see Table 1).

This clinical study was agreed by the European Cancer and Environment Research Institute (ECERI) Scientific/Ethical advisory committee and was conducted according to currently accepted ethical guidelines, including informed written consent approval which was signed by all patients prior to the study. This non-invasive investigation has been also registered in the European Clinical Trials Database (EudraCT) under the registration number 2017-003937-27.

FPP Treatment and Study Design

FPP was supplied by Osato research institute as sachets containing 4.5 g of powder, and administered one sachet at once, twice daily (morning and evening), according to the recommended dose (9 g/day) in the trial of this commercially available FPP product, during 6 months. The FPP components have been previously reported in Aruoma O I et al., Toxicology. 2010, 278:6-16.

The study was an open prospective case-crossover phase I-II study, each patient serving as its own control over time. A minimum of one-month washout period between a study inclusion time (Ti) and therapeutic protocol initiation time (T0) was provided in a case of previously treated patients in order to avoid any bias due to an eventual backward effect of a treatment prior to participation in this study.

Additionally, patients were asked to maintain usual lifestyle in order to avoid any confounding factors which may have modified clinical symptoms during the study period. Ordinary diet, physical activity, regular living behavior, and working activity of patients were systematically recorded and carefully analyzed during the study quality assurance process.

Evaluation

Patients were serially investigated clinically and biologically at Ti and T0, after the 3-month treatment (T3) and 6-month treatment (T6). Clinical evaluation was conducted systematically at T3 and T6 in comparison with T0 during a specific face to face interview by using a validated pre-established questionnaire and a complete clinical test. The evaluation included FPP tolerance and clinical effects on EMFIS symptoms. Clinical evaluation was performed using a symptomatic grading scale system:

Grade 0: No symptoms;
Grade 1: Mild and/or transitory symptoms;
Grade 2: Intensive or permanent symptoms; and
Grade 3: Intensive and permanent symptoms.

A shift from Grade 2 and 3 to Grade 0 was considered a "major" symptomatic improvement, while a shift from Grade 3 to Grade 2 or from Grade 2 to Grade 1 was categorized as a "minor" improvement.

Overall clinical response at T3 or T6 was evaluated in comparison with T0 by using the following grading system:
Complete response (CR): Disappearance of all symptoms (that is, Grade 0);
Partial response (PR): Persistence of Grade 1 symptoms;
Stable (S): No change; and
Failure (F): Increase of Grade 2 or 3 symptoms.

A complete biological evaluation was conducted at T3 and/or T6 in comparison with Ti or T0. The biological evaluation included a PI measurement at T3 or T6 by UCTS for comparison with that of Ti; a dosage of EMFIS-related inflammation-related biomarkers in the peripheral blood (that is, histamine, protein S100B, chaperone proteins Hsp27 and Hsp70); and a dosage of oxidative stress-related biomarkers.

Ultrasonic Cerebral Tomosphygmography (UCTS)

After intracranial pulsation measurements were pioneered in the USA, UCTS was standardized and developed in France. In this study, intracerebral tissue-related ultrasonic technique of the related art was rehabilitated to measure precise PI in the two temporal lobes. This is because that preliminary clinical data have revealed that patients complaining with EHS most often have concentration deficiencies (impaired concentration) and the like, in addition to loss of short term memory, frequent auditory or olfactory abnormality.

The UCTS technique has been documented in Belpomme D, Campagnac C, Irigaray P. Reliable disease biomarkers characterizing and identifying electrohypersensitivity and multiple chemical sensitivity as two etiopathogenic aspects of a unique pathological disorder. Rev Environ Health. 2015, 30:251-271 and in Belpomme D, Hardell L, Belyaev I, Burgio E, Carpenter D O. Thermal and non-thermal health effects of low intensity non-ionizing radiation: An international perspective. Environ Pollut. 2018 November; 242(Pt A):643-658. The UCTS includes a non-invasive computerized technique that enables measurement of mean tissue PI by centimeter-thick sections of the temporal lobes from the cortex to the middle line of the brain by using the emission of 2 MHz pulsed ultrasonic waves at different intensity levels from a transmitting ultrasonic source (see FIG. 1), in addition to the analysis of the reflection of these ultrasonic waves on the different neurologic and vascular tissue structures in the temporal lobes, particularly the red blood cells (RBC) in capillaries of the vascular network of the middle cerebral artery (MCA).

FIG. 1 is a schematic diagram showing the different middle cerebral artery (MCA)-dependent areas individualized in the temporal lobes for the measurement of mean PI by using the UCTS according to Parini et al, Agressologie. 1984, 25:585-589. The addition of the mean PI value obtained at 3 cm ($3^{rd}$ cm) from the cutaneous cranial surface to the mean PI value obtained at the 4 cm ($4^{th}$ cm) corresponds to a cortical/sub-cortical area. The addition of the mean PI values obtained from 3 cm ($3^{rd}$ cm) to the 5 cm ($5^{th}$ cm) corresponds to the surface area of the MCA (superficial MCA). The addition of the mean PI values obtained from the 5 cm ($5^{th}$ cm) to the 7 cm ($7^{th}$ cm) corresponds to a deep area of MCA (deep MCA) and the mean PI value obtained at the 7 cm corresponds to the capsulo-thalamic area. The addition of values obtained from the 3 cm to the 7 cm corresponds to the MCA dependent carotidian area. Finally, the addition of values obtained from the 8 cm to the 9 cm corresponds to the vertebro-basilar area.

The mean PI values corresponding to the different temporal lobe territories investigated were directly recorded by a used standard UCTS equipment. As a result, by using the UCTS, it was possible to measure the mean PI in each of the different tissue territories in all patients. The present inventors determined the mean PI values in each of the six individualized temporal lobe territories with respect to the analysis of 727 EHS and/or MCS patients and compared these values to a series of normal historical controls that have been used as the physiological mean PI reference values (Parini M et al. Application in 143 healthy subjects. Agressologie. 1984, 25:585-589.). Through this, it was possible to show that in comparison to normal subjects, cerebral pulsatility in patients with self-reporting EHS decreased in the capsulo-thalamic area in most cases or was even completely suppressed, in several tissue areas in one or two temporal lobes. Within these territories, brain blood flow may be decreased in EHS and/or MCS patients (Belpomme D, Campagnac C, Irigaray P. Reliable disease biomarkers characterizing and identifying electrohypersensitivity and multiple chemical sensitivity as two etiopathogenic aspects of a unique pathological disorder. Rev Environ Health. 2015, 30:251-271.).

Therefore, in the present study, the UCTS was used to measure PI at T0, T3, and/or T6 in the temporal lobes i.e. before and after FPP administration in order to examine whether FPP is able to restore normal PI.

Inflammation and Oxidative Stress Related Biomarkers

One objective of this study was to measure oxidative stress and oxidative stress-related low grade inflammation by using specific biomarkers in the peripheral blood of EMFIS-bearing patients before and after FPP treatment in order to demonstrate the possibility of FPP anti-inflammatory and anti-oxidative stress effects.

Blood Collection

Venous whole blood sampling was performed at Ti, T0, T3, and T6 in laboratory "Labo XV" in Paris. The EHS-related biomarkers were measured in this laboratory on serum, with the exception of histamine, which was measured on plasma after a whole blood collection on lithium heparinate. For oxidative stress-related biomarkers, whole blood was also collected on lithium heparinate and frozen immediately at −80° C. Then, the samples were sent to Laboratory Equinox (France) specialized in oxidative stress measurement and analysis in the University Hospital of Grenoble.

Inflammation-Related Biomarkers

The methods of measurement of the inflammation-related biomarkers used in this study have already been known (for example, Belpomme D, Campagnac C, Irigaray P. Reliable disease biomarkers characterizing and identifying electrohypersensitivity and multiple chemical sensitivity as two etiopathogenic aspects of a unique pathological disorder. Rev Environ Health. 2015, 30:251-271.). For histamine, an ELISA specific test (Histamine ELISA RE59221 from IBL International GmbH) was used, and for protein S100B, a quantitative automated chemiluminescent immunoassays (Liason S100 from DiaSorin Deutschland GmbH) was used. For the chaperone protein Hsp27, a quantitative sandwich ELISA assay test (Assay Designs (trade mark) Hsp27 ELISA kit) was used, and for the chaperone protein Hsp70, an Enzyme Immunometric Assay test (Assay Designs (trade mark) Hsp70 High Sensitivity Enzyme Immunometric Assay kit) was used. All tests were performed using commercially available reagents, each patient value was compared to the normal reference value obtained from the commercial companies. Sensitivity, specificity, and reproducibility of the tests were in agreement with those provided by the companies. All assays were performed according to the recommended manufacturer's method.

Oxidative and Antioxidative Stress-Related Biomarkers

A series of tests was used to measure oxidative stress biomarkers and anti-oxidative enzyme and enzyme proteins in plasma and/or red blood cells before and after FPP treatment (Table 1). Centrifugation (4000 g, 10 min, 4° C.) was performed to separate the RBC from the plasma. Normal reference values obtained for each biomarker used in this study were pre-determined from the analysis of a series of 123 normal subjects.

Oxidative Stress Biomarkers

For the oxidative stress evaluation, the three following types of markers in the plasma were used: malondialdehyde (MDA); all thiobarbituric acid (TBA); and thiobarbituric acid reactive substances (TBARS), and total thiol group proteins (Table 1).

For measuring the MDA, reaction with TBA was used. The MDA-TBA complex was then separated from interfering substances and specifically identified by using reverse-phase HPLC coupled with a UV/visible detection. In fact, MDA was quantified on the basis of strong light absorbing and fluorescing property thereof following the reaction with TBA (Ohkawa H et al. Anal Biochem. 1979, 95:351-358). Results were expressed in μmoles (μM) per liter.

For the dose of lipid peroxidation intermediates, all plasma TBARS was measured by using a modification of the method of Ohkawa et al. This method is based on the reaction of the aldehyde function of TBARS with TBA to form a TBARS-TBA colored complex which was quantified by fluorometry. Results were expressed in μM. For the dosage of total thiol (SH) group proteins, 5,5'-dithio-bis(2-nitrobenzoic acid) (DTNB) was used as reagent and the level of plasmatic SH group was measured spectrophotometrically at 412 nm (Jocelyn P C et al. Methods Enzymol. 1987, 143:44-67). Results were expressed in Unit per liter (U/l).

Antioxidative Non-Enzymatic Proteins

The dosage of reduced glutathione (GSH) and oxidized glutathione (GSSG) in the plasma was determined according to the method of Akerboom et al. Methods Enzymol. 1981, 77:373-382. Briefly, centrifuged (400 g, for 10 min, at 4° C.) 400 μl of whole blood were collected in 3.6 ml of metaphoric acid. After the centrifugation, total glutathione and GSH were measured enzymatically in the acidic proteinfree-supernatant. The assay of GSSG was performed after having masked GSH by adding 2-vinylpyridine to the deproteinized extract. As for the total glutathione and GSH, the GSSG was measured enzymatically. Results were expressed in μM.

Finally, measurement of the total antioxidant status (TAS) in the plasma was performed by a colorimetric method using a randox kit (Randox Total Antioxidant Status, NX2332, Randox laboratory) (Miller N J et al., Clin Sci (Lond). 1993, 84:407-412). Results were expressed in μM.

Antioxidative Enzymatic Proteins

Measurement of antioxidative enzymes was performed in RBC or both in RBC and plasma. For measuring Cu—Zn superoxide dismutase (SOD) activity in the RBC, the method described by Marklund S et al., Eur J Biochem. 1974, 47:469-474, which is a simple and rapid test based on the ability of SOD to inhibit the autoxidation of Pyrogallol. In fact, at pH 7.9 the reaction is inhibited by SOD, indicating the almost total effect of SOD on the superoxide anion radical and $O_2^{\circ -}$, in the reaction. In this method, the rate of pyrogallol auto-oxidation was measured spectrophotometrically from the increase in absorbance at 420 nm. One unit of SOD activity was defined as the dosage of the enzyme required to inhibit the rate of pyrogallol auto-oxidation by 50%. Results were expressed in Unit/mg hemoglobin (U/mg Hb).

For the dosage of glutathione reductase (GR), a colorimetric method from a randox kit (GR2368 from Randox laboratory) (Mannervik B et al. Curr Protoc Toxicol. 200: 10.1002/0471140856.tx0702s00). Results were expressed in Unit/g of hemoglobin (U/g Hb) for a case of RBC GR, and in Unit per liter (U/l) for a case of plasmatic GR.

Additionally, for glutathione peroxidase (GPx) activity, a method described in Gunzler et al., Z Klin Chem Klin Biochem. 1974, 12: 444-448 was used. The GPx assay was based on the oxidation of NADPH to NADP+, which is accompanied by a decrease in absorbance at 340 nm. A rate of this decrease is directly proportional to the GPx activity in the sample. The GPx activity was evaluated in nmoles per liter (nM) of NADPH oxidized per min and the results were expressed in Unit/g of hemoglobin (U/g Hb) for a case of RBC GPx and in Unit per liter (U/L) for a case of plasmatic GPx.

TABLE 1

Various studied biomarkers

| | Biomarkers | Sample |
|---|---|---|
| Inflammation-related biomarkers | Histamine | Plasma |
| | Protein S100B | Serum |
| | Protein Hsp27 | Serum |
| | Protein Hsp70 | Serum |
| Oxidative stress biomarkers | Malondialdehyde (MDA) | Plasma |
| | Thiobarbituric acid reactive substances (TBARS) | Plasma |
| | Total thiol group | Plasma |

TABLE 1-continued

Various studied biomarkers

| | Biomarkers | Sample |
|---|---|---|
| Antioxidative non-enzymatic proteins | Oxidized glutathione (GSSG) | Plasma |
| | Reduced glutathione (GSH) | Plasma |
| | Total glutathione | Plasma |
| | Total antioxidant status (TAS) | Plasma |
| Antioxidative enzymes | Superoxide dismutase (SOD) | RBC |
| | Glutathione reductase (GR) | Plasma |
| | Glutathione reductase (GR) | RBC |
| | Glutathione peroxidase (GPx) | Plasma |
| | Glutathione peroxidase (GPx) | RBC |

Statistical Analysis

The design of this study was a case-crossover clinical study, which includes a within group comparison between the data obtained before and after the treatment.

Clinical evaluation before and after the FPP treatment was described as the following. Major side effect and minor symptomatic improvements in addition to the overall response rates were established according to the clinical criteria previously defined in the section "Evaluation".

Three different statistical tests were used:
(1) The Chi-squared test of independence for comparison between the percentages of patients for the symptomatic (Tables 2 and 3) and biomarker evaluation (Table 6);
(2) The Fisher exact test followed by the two-tailed Student's t test for comparison between the values obtained from two groups under comparison, such as the mean PI values relative to the mean normal control values (Table 5), or between the values obtained for the various oxidative stress-related biomarkers obtained from the patients without oxidative stress relative to the patients with oxidative stress (Table 8); and
(3) The Wilcoxon signed-rank test (hypothesized as not in agreement with a normal distribution for a within group comparison between the different values obtained at time measurement, such as for PI (Table 5) or biomarker analysis (Tables 7 and 9)).

All statistical analysis was conducted using XLSTAT software.

Results

Among the 32 patients, 26 persons were evaluable both for clinical symptoms and biological studies at T3. 5 cases were lost in the follow-up period between Ti and T3 and 1 case was not evaluable. At T6, 18 patients were evaluable, 4 cases were excluded from the protocol at T3, and 4 other cases were lost in the follow-up period between T3 and T6.

Clinical Evaluation

In this study, all evaluable patients tolerated FPP well. Tables 2, 3, and 4 summarize the clinical data.

Major symptomatic improvement at T3 was obtained in 20 to 40% of cases for loss of short term memory, impaired concentration/attention deficit, insomnia, and fatigue. In contrast, there was improvement in only 5 to 15% of cases for depressive tendencies and for neurologic symptoms, such as headache, tinnitus, and dysesthesia. However, when including the minor improvement, the total symptomatic improvement reaches approximately 30 to 60% of the cases, depending on a type of symptoms analyzed, which persists at T6 for those patients who reached 6 month FPP treatment (Table 2).

TABLE 2

Symptomatic evaluation at T3 and T6 in comparison with T0

| | T3(n = 26) | | | T6(n = 18) |
|---|---|---|---|---|
| Symptoms | Major improvement | Minor improvement | Total improvement | Total improvement |
| Headache | 2/26 (7.7%) | 12/26 (46.2%) | 14/26 (53.9%) | 8/18 (44.4%) |
| Fatigue | 11/26 (42.3%) | 7/26 (26.9%) | 18/26 (69.2%) | 14/18 (77.8%) |
| Impaired concentration | 10/26 (38.5%) | 6/26 (23.1%) | 16/26 (61.5%) | 14/18 (77.8%) |
| Loss of short term memory | 5/26 (19.2%) | 9/26 (34.6%) | 14/26 (53.8%) | 10/18 (55.6%) |
| Attention deficit | 7/26 (26.9%) | 6/26 (23.1%) | 13/26 (50%) | 11/18 (61.1%) |
| Tinnitus | 2/26 (7.7%) | 7/26 (26.9%) | 9/26 (34.6%) | 7/18 (38.9%) |
| Insomnia | 5/26 (19.2%) | 7/26 (26.9%) | 12/26 (46.2%) | 7/18 (38.9%) |
| Depression tendency | 3/26 (11.5%) | 7/26 (26.9%) | 10/26 (38.5%) | 14/18 (77.8%) |
| Dysesthesia | 2/26 (7.7%) | 8/26 (30.8%) | 10/26 (38.5%) | 11/18 (61.1%) |

Table 3 shows percentages of patients with symptoms at T3 and T6 in comparison with T0 are statistically significantly decreased for each symptom analyzed (p<0.0001).

TABLE 3

Evaluation of the percentage of patients at T3 and T6 in comparison with T0 for each symptom analyzed

| | Percent of patients with symptoms (%) | | | P value* | |
|---|---|---|---|---|---|
| Symptoms | T0 | T3 | T6 | T3/T0 | T6/T0 |
| Headache | 90.63 | 46.88 | 65.63 | <0.0001 | <0.0001 |
| Fatigue | 90.63 | 34.38 | 46.88 | <0.0001 | <0.0001 |
| Impaired concentration | 81.30 | 31.30 | 37.50 | <0.0001 | <0.0001 |
| Loss of short term memory | 84.38 | 40.63 | 53.13 | <0.0001 | <0.0001 |
| Attention deficit | 81.25 | 40.63 | 46.88 | <0.0001 | <0.0001 |
| Tinnitus | 65.63 | 37.50 | 43.75 | <0.0001 | <0.0001 |
| Insomnia | 59.38 | 21.88 | 37.50 | <0.0001 | <0.0001 |
| Depression tendency | 56.25 | 25.00 | 12.50 | <0.0001 | <0.0001 |
| Dysesthesia | 53.13 | 28.13 | 9.38 | <0.0001 | <0.0001 |

*p values relative to T0 values were calculated using the Chi-square test of independence Finally, a complete or partial clinical response was obtained at T3 in 14 cases of the 26 evaluable cases which resulted in an overall response rate of 53.8% (Table 4).

TABLE 4

Overall clinical response rates after 3 month FPP treatment (T3) in the 26 evaluable patients

| Response | Number of patients | |
|---|---|---|
| Non-evaluable | 6/32 (18.8%) | |
| Evaluable | 26/32 (81.2%) | |
| Complete response | 3/26 (11.5%) | 14/26 (53.8%) |
| Partial response | 11/26 (42.3%) | |
| Stability | 8/26 (30.8%) | 12/26 (46.2%) |
| Failure | 4/26 (15.4%) | |

UCTS

Figure 2:
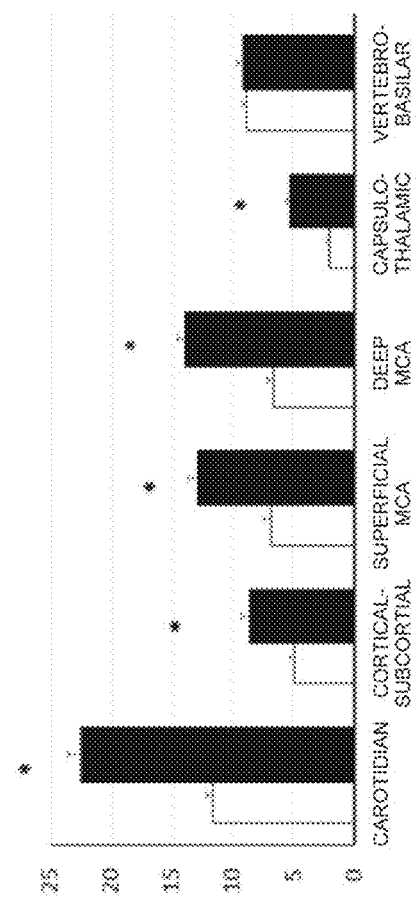
FIG. 2 is graphs showing comparison of mean pulsometric indices (PI) measured by UCTS in different territories of right temporal lobes between the time of study initiation T0 and after 3 months T3 (white) or after 6 months T6 (black).
Figure 3:
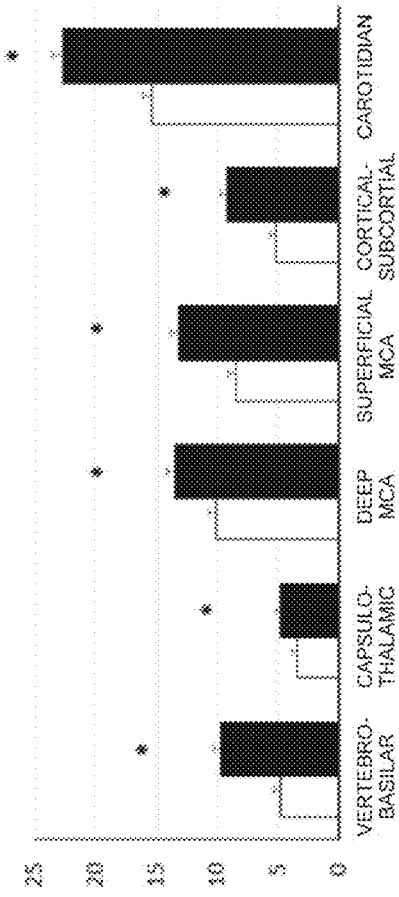
FIG. 3 are graphs showing comparison of mean pulsometric indices (PI) measured by UCTS in different territories of left temporal lobes between the time of study initiation T0 and after 3 months T3 (white) or after 6 months T6 (black).

As indicated in Table 5 and FIGS. 2A and 2B, it was confirmed that by using UCTS at Ti, there was a statistically significant decrease in mean PI value in the capsulo-thalamic area of right and left temporal lobes and in the deep MCA area and the vertebro-basilar area of the both temporal lobes respectively. On the other hand, there was a statistically significant increase in the cortical/subcortical and superficial MCA areas in the right and left temporal lobes. At T3/T6, a statistically significant recovery of normal mean PI value in comparison to Ti for the capsulo-thalamic area of both temporal lobes, and for the deep MCA area and the vertebro-basilar area of the right and left temporal lobes respectively was found.

Accordingly, with exception of the vertebro-basilar area of the right temporal lobe which shows no PI recovery, in all tissue areas for which there was a decreased mean PI value at Ti, it was recovered at T3/T6 up to a statistically significant normal mean PI value after FPP treatment. In contrast, for all the other tissue areas with a normal or increased mean tissue PI value at Ti, the mean PI values at T3/T6 were statistically significantly increased.

FIGS. 2A and 2B show mean PI values recorded by UCTS in the different territories of each of the right and left temporal lobes investigated at T3/T6 in comparison with Ti. FIG. 2A shows right temporal lobe and FIG. 2B shows left temporal lobe. White columns correspond to mean values ±SD at Ti and black columns correspond to mean values ±SD at T3/T6. * shows statistically significant values using the Wilcoxon signed-rank test.

Inflammation-Related Biomarkers

Tables 6 and 7 show the results obtained at T3 and T6 in comparison with Ti for the inflammation-related biomarkers in EHS-bearing patients presenting with increase in these biomarkers at Ti.

As shown in Table 6, there is a statistically significant decrease in the number and percentage of EHS patients with abnormal inflammation-related biomarker values at T3 and T6 in comparison with Ti ($p<0.0001$) for histamine, S100B protein, and HSP27/HSP70 chaperone proteins. This suggests the occurrence of FPP-related anti-inflammatory effect in the peripheral blood of EHS patients with initially detectable inflammation. Moreover, as shown in Table 7, the FPP-related anti-inflammatory effect was confirmed by comparing the mean values ±SD of histamine and Hsp27/Hsp70 chaperone proteins at T3 and T6 with values at Ti, the decrease in mean values ±SD being statistically significant at T3 and T6 relative to Ti.

TABLE 5

Mean PI values (±SD) measured in the different MCA dependent tissue territories in the left and right temporal lobes

| | Tissue sections | Reference values | Ti | T3/T6 | D %*** | P-value**** |
|---|---|---|---|---|---|---|
| Right temporal lobe | Carotidian | 13 ± 2 | 11.60 ± 2.80 | 22.52 ± 5.26 | 94.20 | <0.0001 |
| | Cortical-subcortial | 1.5 ± 0.5 | 4.89 ± 2.31* | 8.61 ± 3.46 | 75.83 | <0.0005 |
| | Superficial MCA | 5 ± 1 | 6.88 ± 2.70* | 12.86 ± 4.10 | 86.73 | <0.0001 |
| | Deep MCA | 12 ± 2 | 6.69 ± 2.20** | 13.91 ± 3.10 | 107.90 | <0.0001 |
| | Capsulo-thalamic | 5 ± 1 | 2.02 ± 0.86** | 5.28 ± 1.63 | 160.93 | <0.0001 |
| | Vertebro-basilar | 9 ± 1 | 8.87 ± 1.59 | 9.15 ± 2.37 | 3.25 | 0.2636 |
| Left temporal lobe | Vertebro-basilar | 9 ± 1 | 4.79 ± 2.86** | 9.70 ± 2.79 | 102.61 | <0.0001 |
| | Capsulo-thalamic | 5 ± 1 | 3.46 ± 1.68** | 4.77 ± 2.03 | 37.78 | 0.0151 |
| | Deep MCA | 12 ± 2 | 10.12 ± 2.67 | 13.42 ± 3.40 | 32.70 | 0.0018 |
| | Superficial MCA | 5 ± 1 | 8.48 ± 3.30* | 13.16 ± 3.03 | 55.22 | <0.0001 |
| | Cortical-subcortical | 1.5 ± 0.5 | 5.18 ± 2.33* | 9.21 ± 2.25 | 77.74 | <0.0001 |
| | Carotidian | 13 ± 2 | 15.30 ± 4.00 | 22.63 ± 4.40 | 47.96 | <0.0001 |

*Mean PI values at Ti relative to normal reference values are statistically significantly increased using the Fisher exact test followed by the two-tailed Student's t-test ($p < 0.001$).

**Mean PI values at Ti relative to normal reference value are statistically significantly decreased using the Fisher exact test followed by the two-tailed Student's t-test. ($p < 0.0001$ for the capsulo-thalamic area and the deep MCA area of the right temporal lobe and for the vertebro-basilar area of the left temporal lobe, while being $p < 0.01$ for the capsulo-thalamic area of the left temporal lobe.).

***D % is calculated according to $((t3/t6 - ti)/ti) \times 100\%$, and corresponds to the percent mean value change between T3/T6 and Ti.

****p values for comparison between mean PI values obtained at T3/T6 and Ti were calculated using the Wilcoxon signed-rank test.

TABLE 6

Number and percentage of EHS-bearing patients with increased inflammation-
related biomarker values at T3 and T6 in comparison with Ti

| | Reference values | Ti | T3 | T6 | P value* T3/Ti | P value* T6/Ti |
|---|---|---|---|---|---|---|
| Histamine | 10 nmol/l | 11 (42.3%) | 4 (15.4%) | 3 (16.7%) | <0.0001 | <0.0001 |
| S100B | 0.105 µg/l | 6 (23.1%) | 3 (11.5%) | 0 | 0.03 | <0.0001 |
| Hsp27/Hsp70 | 5 ng/ml | 17 (65.4%) | 5 (19.2%) | 2 (11.1%) | <0.0001 | <0.0001 |

*p values relative to Ti were calculated using the Chi-square test of independence

TABLE 7

Mean values (±SD) of inflammation-related biomarkers at T3 and T6 in comparison with Ti
in EHS-bearing patients having initial detectable increased inflammation-related biomarkers.

| | Reference values | Ti | T3 | T6 | P value* T3/Ti | P value* T6/Ti |
|---|---|---|---|---|---|---|
| Histamine | 10 nmol/l | 23.22 ± 9.79 | 12.03 ± 11.90 | 8.73 ± 8.06 | 0.049 | 0.006 |
| S100B | 0.105 µg/l | 0.188 ± 0.104 | 0.097 ± 0.002 | 0.08 ± 0.02 | 0.142 | 0.098 |
| Hsp27/Hsp70 | 5 ng/ml | 9.02 ± 7.41 | 4.29 ± 1.76 | 3.34 ± 1.98 | 0.007 | <0.001 |

*Comparison was performed using the Wilcoxon signed-rank test.

Oxidative Stress and Antioxidative Stress-Related Biomarkers

Results are shown in Tables 8 and 9. A remarkable finding is that 12 persons (46%) of the 26 evaluable patients experienced oxidative stress. At T0, these patients presented with statistically significant increase in MDA and TBARS in the plasma relative to the normal reference values, while these values differed statistically significantly from those obtained in the patients with no detectable oxidative stress ($p<0.0001$). Moreover, in comparison with normal reference value, the individualization of patients with oxidative stress from patients with no oxidative stress was statistically significantly increased in oxidative stress bearing patients ($p<0.0001$), but not increased in patients with no oxidative stress (Table 8).

TABLE 8

Individualization and characterization of EHS self-reporting patients with oxidative
stress at T0 and comparison between the two groups with or without oxidative stress.

| Oxidative stress Biomarkers | Normal reference values | Patients with oxidative stress (n = 12) | Patients without oxidative | P value** |
|---|---|---|---|---|
| MDA | 1.47 ± 0.35 µµM | 2.14 ± 0.17* | 1.53 ± 0.21 | <0.0001 |
| TBARS | 2.5 ± 0.37 µM | 3.16 ± 0.18* | 2.67 ± 0.23 | <0.0001 |
| Total thiol group | 6.79 ± 0.99 µmoles/g | 6.56 ± 0.46 | 6.51 ± 0.44 | 0.74 |
| GSSG | 12.40 ± 6.90 µM | 24.08 ± 12.66* | 18.74 ± 7.37 | 0.14 |
| GSH | 966 ± 237 µM | 848.38 ± 160.18 | 822.12 + 149.47 | 0.64 |
| Total glutathione | 988.50 ± 239.50 µM | 896.58 ± 175.40 | 859.60 ± 148.79 | 0.53 |
| GSH/Total glutathione ratio | 97 ± 2.90% | 94.75 ± 1.99 | 95.54 ± 1.75 | 0.25 |
| GSH/GSSG ratio | 97.55 ± 57.45 µM/µM | 41.20 ± 15.75 | 50.35 ± 23.02 | 0.23 |
| TAS | 1.50 ± 0.15 µM | 1.46 ± 0.05 | 1.47 ± 0.09 | 0.73 |
| SOD | 1.34 ± 0.12 U/mgHb | 1.47 ± 0.14 | 1.51 ± 0.09 | 0.42 |
| PlasmaGR | 54 ± 21 U/l | 65.42 ± 8.22 | 60.50 ± 9.03 | 0.14 |
| RBCGR | 8.95 ± 4.25 U/g Hb | 9.83 ± 1.28 | 9.18 ± 2.23 | 0.36 |
| PlasmaGPx | 375 ± 75 U/l | 399.00 ± 33.86 | 367.45 ± 58.80 | 0.10 |
| RBCGPx | 44.15 ± 16.35 U/g Hb | 53.53 ± 10.80 | 50.95 ± 8.18 | 0.45 |

*Mean values ±SD are statistically significantly increased more than the normal values ($p < 0.0001$).

**For comparison between patients with oxidative stress and patients without oxidative stress, p values were calculated by using the Fisher exact test followed by the two-tailed Student's t-test.

TABLE 9

FPP-related antioxidative response at T3 in comparison with T0
in EHS self-reporting patients with or without oxidative stress

| Oxidative stress biomarkers | Patients with oxidative stress | | | Patients without oxidative stress | | |
|---|---|---|---|---|---|---|
| | T0 | T3 | P value** | T0 | T3 | P value** |
| MDA | 2.14 ± 0.17* | 1.82 ± 0.17 | <0.001 | 1.54 ± 0.23 | 1.44 ± 0.29 | 0.28 |
| TBARS | 3.16 ± 0.18* | 3.01 ± 0.26* | 0.13 | 2.65 ± 0.24 | 2.58 ± 0.33 | 0.47 |
| Total thiol group | 6.56 ± 0.46 | 6.50 ± 0.39 | 0.67 | 6.53 ± 0.47 | 6.60 ± 0.39 | 0.60 |
| GSSG | 24.08 ± 12.66* | 23.26 ± 10.97* | 0.73 | 19.57 ± 7.98 | 18.73 ± 6.32 | 0.60 |
| GSH | 848.38 ± 160.18 | 852.85 ± 123.68 | 0.85 | 828.81 ± 136.72 | 761.41 ± 157.05 | 0.19 |
| Total glutathione | 896.58 ± 175.40 | 899.33 ± 142.76 | 0.97 | 867.87 ± 135.80 | 798.87 ± 158.15 | 0.15 |
| GSH/Total glutathione ratio | 94.75 ± 1.99 | 95.02 ± 1.62 | 0.58 | 95.43 ± 1.82 | 95.15 ± 1.97 | 0.60 |
| GSH/GSSG ratio | 41.20 ± 15.75 | 42.01 ± 13.69 | 0.85 | 49.12 ± 23.48 | 45.70 ± 18.84 | 0.72 |
| TAS | 1.46 ± 0.05 | 1.46 ± 0.08 | 0.76 | 1.45 ± 0.07 | 1.46 ± 0.11 | 1 |
| SOD | 1.47 ± 0.14 | 1.51 ± 0.14 | 0.22 | 1.49 ± 0.08* | 1.52 ± 0.09* | 0.12 |
| Plasma GR | 65.42 ± 8.22 | 66.83 ± 8.67 | 0.29 | 61.07 ± 10.03 | 60.80 ± 11.71 | 0.21 |
| RBC GR | 9.83 ± 1.28 | 9.97 ± 2.09 | 0.85 | 8.67 ± 1.86 | 9.16 ± 2.08 | 0.15 |
| Plasma GPx | 399.00 ± 33.86 | 378.70 ± 125.95 | 0.57 | 365.73 ± 42.80 | 382.13 ± 38.90 | 0.06 |
| RBC GPx | 53.53 ± 10.80 | 56.22 ± 11.05 | <0.01 | 52.46 ± 7.80 | 48.37 ± 17.58 | 0.45 |

*Mean values ±SD were statistically significantly increased by using the Fisher's exact test followed by the two-tailed Student's t-test (p < 0.0001).
**p values were calculated using the Wilcoxon signed-rank test.

As shown in Table 9, for the group of patients with oxidative stress at T3 in comparison with T0, a statistically significant decrease of MDA level in the plasma (p<0.0001) and a statistically significant increase in the glutathione peroxidase activity in red blood cells (p<0.01) were confirmed. This result suggests that FPP may have some detectable antioxidative effect in patients with initially detectable oxidative stress.

Conclusion

Overall, clinical improvement was obtained in 50 to 60% of the cases, among which 20 to 35% presented mainly the reduction of cognitive symptoms such as loss of short term memory, impaired concentration, attention deficit, insomnia, and fatigue. This clinical improvement was objectively supported by a statistically significant normal recovery of mean intracerebral tissue PI in the temporal lobes and by an FPP-related antioxidative effect, evidenced by a statistically significant decrease in malondialdehyde levels in the plasma (p<0.0001) and increase in the Glutathione peroxidase activity in red blood cells (p<0.01) in patients experiencing oxidative stress. Moreover, this study evidenced a certain degree of FPP-related anti-inflammatory effects by demonstrating a statistically significant decrease in histamine (p=0.049) and HSP27/HSP70 chaperone proteins (p=0.007) in the peripheral blood. The result suggests a beneficial clinical and biological therapeutic effect of FPP in EHS self-reporting patients. The FPP is an effective therapeutic agent for EMFIS-bearing patients, that is, so-called EHS self-reporting patients.

The FPP is expected to contribute to the establishment of therapy for "environmental disease" caused by environmental factors, such as "electrohypersensitivity" or "chemical sensitivity" which will increase in future.

What is claimed is:

1. A method of treating electrohypersensitivity in a subject in need thereof, comprising administering an effective amount the pharmaceutical composition comprising a fermented *papaya* preparation.

2. The method according to claim 1, which is for a suppression of a decrease in brain blood flow.

3. The method according to claim 1, which is for a reduction of cognitive impairment, somnipathy, and/or fatigue.

4. The method according to claim 3, wherein the cognitive impairment includes loss of short term memory, impaired concentration, and attention deficit.

5. The method according to claim 1, wherein the subject is human.

6. The method according to claim 1, wherein the subject is not diagnosed with type 2 diabetes.

7. The method according to claim 1, in which the subject is not diagnosed with diabetes.

8. The method according to claim 1, wherein the subject is not in need of an antioxidant.

9. The method according to claim 1, wherein subject is not diagnosed with any inflammatory disease.

10. The method according to claim 1, wherein subject is not diagnosed with any immune disease.

11. The method according to claim 1, wherein the subject has clinical symptoms associated with electrohypersensitivity comprising cognitive impairment, somnipathy, and/or fatigue.

12. The method according to claim 1, in which a dose of the fermented papaya preparation is 0.5 to 30 g/day for adults weighing 70 kg.

* * * * *